(12) United States Patent
Joshi et al.

(10) Patent No.: US 6,608,206 B1
(45) Date of Patent: Aug. 19, 2003

(54) PROCESS FOR MAKING S(-) AMLODIPINE SALTS

(75) Inventors: Rohini Ramesh Joshi, Pune (IN);
Ramesh Anna Joshi, Pune (IN);
Mukund Keshav Gurjar, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/283,762

(22) Filed: Oct. 30, 2002

(51) Int. Cl.⁷ .............................................. C07D 211/86
(52) U.S. Cl. ....................................................... 546/321
(58) Field of Search ......................................... 546/321

(56) References Cited

U.S. PATENT DOCUMENTS 5,438,145 A  *  8/1995  Furlan et al. ................ 546/321
6,046,337 A  *  4/2000  Bozsing et al. ............. 546/321
6,476,058 B2 *  11/2002 Foster ......................... 514/356

* cited by examiner

*Primary Examiner*—Patricia L. Morris
(74) *Attorney, Agent, or Firm*—Luedeka, Neely & Graham PC

(57) ABSTRACT

A process for the preparation of S(−) Amlodipine salts which comprises reaction of S(−)Amlodipine base with a solution of pharmaceutically acceptable acid such as benzene sulfonic acid, oxalic acid, maleic acid, succinic acid and p-toluene sulfonic acid. The reaction is carried out in the presence of an organic solvent at room temperature. The organic solvents include alcohols like ethanol methanol 2 propanol hydrocarbons like toluene and polar solvent like dimethyl sulfoxide. The salt is obtained by addition of water and isolation of the salt formed by filtration. The unique feature of the invention is production of S(−) Amlodipine besylate in good chemical yield, high enantiomeric purity and with the quality required for preparation of pharmaceutical composition i.e. tablet formulation.

6 Claims, No Drawings

PROCESS FOR MAKING S(-) AMLODIPINE SALTS

FIELD OF THE INVENTION

This invention relates to a process for the preparation of S(–) Amlodipine salts. More particularly it relates to the process for the preparation of pharmaceutically acceptable salts of S(–)Amlodipine such as besylate, succinate, maleate, oxalate and tosylate. The S (–) Amlodipine salts of general formula (1)

FORMULA (1)

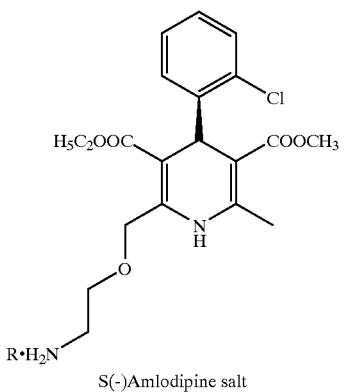

S(-)Amlodipine salt

Wherein R=Benzene sulfonic acid, succinic acid, maleic acid, oxalic acid and p-toluene sulfonic acid.

BACKGROUND AND SUMMARY OF THE INVENTION

Salts of S(–) Amlodipine are prepared as per the procedure of the present invention from S (–) Amlodipine, the procedure for the preparation of the S(–) Amlodipine has been fully described and claimed in co-pending Indian patent application No. NF 383/2001.

Of all the salts of S (–) Amlodipine mentioned above, the compound S (–) Amlodipine besylate; (4-S)-2-{[(2-aminoethyl)oxy]methyl}-4-(2-chlorophenyl)-6-methyl-1,4-dihydropyridine-3,5-dicarboxylate benzene sulfonate has commercial importance and is a potent and long acting calcium channel blocker.

(R,S)-Amlodipine besylate is currently being used for the treatment of cardiovascular disorders, in particular in the treatment of hypertension and angina, Amlodipine is a racemic compound and has chiral center at 4 position of dihydropyridine ring. The S(–) isomer has calcium channel blocker activity while the R(+)-isomer has little or no calcium channel blocking activity.

The compound R,S-Amlodipine is a potent and long acting calcium channel blocker having utility as an anti-ischaenic and anti-hypertensive agent. Although amlodipine is effective as the free base in practice it is best administered in the form of a salt of pharmaceutically acceptable acid, such as hydrochloride, hydrobromide, maleate, fumarate, tartarate and besylate.

Of these salts, besylate is disclosed as being particularly preferred as it has good solubility, good stability, nonhygroscopicity and processability for tablet formation (Ger. Offen.—DE—3710457, (1988), Edward Davison, James Ingram Wells).

In the prior art the preparation of R and S enantiomers of Amlodipine have been reported by resolution of amlodipine azide ester with optically active 2-methoxy-2-phenylethanol (*J. Med. Chem.*, No. 29, p. 1696, (1986). J. E. Arrowsmith, S. F. Campbell, P. E. Cross, J. K. Stabs, R. A. Burges and EP Application No. 0331315A) or resolution of Amlodipine base with optically active camphanic acid (*J Med. Chem.*, No. 35, p. 3341, (1992), S. Goldman, J. Stoltefuss and L. Born) or resolution of RS-amlodipine base to R(+) and S(–) isomer with L or D-tartaric acid respectively in organic solvent DMSO, (Peter L. Spargo U.S. Pat. No. 6,046,338; (2000), PCT 95/25722 (1995) which indicate the use of both tartaric acids is essential.

Preparation of R and S amlodipine maleate salt has been reported starting from azido precursor. The procedure involves resolution of azido precursor using 2-methoxy-2-phenyl ethanol as a resolving agent, separation of diastereomer, ester exchange with sodium methoxide, hydrogenation, chromatographic purification and maleate salt formation. (*J. Med. Chem.*, No. 29, p. 1896, (1986). J. E. Arrowsmith, S. F. Campbell, P. E. Cross, J. K. Stabs, R. A. Burges).

Preparation of preferred amlodipine besylate salt has been disclosed in the publication (*J. Chrom.B* 693 (1997) pp. 367–375, J. Luksa, Dj. Josic, B. Podobnik, B. Furlan, M. Kremser) describing the treatment of ethanolic solution of base with benzene sulfonic acid and isolation. The detailed procedures to obtain these salts have not been provided by the prior art. These prior art references also lack in providing physical or structural data given except the optical rotation except maleate. The main object of the present invention therefore to provide a process for the preparation of S (–) Amlodipine salts.

Another object is to provide the process to obtain the salts in good yields. Yet another object is to obtain the salts with high enantiomeric purity.

DETAILED DESCRIPTION OF THE INVENTION

Accordingly the present invention provides a process for the preparation of S(–) Amlodipine salts of general formula (1)

FORMULA (1)

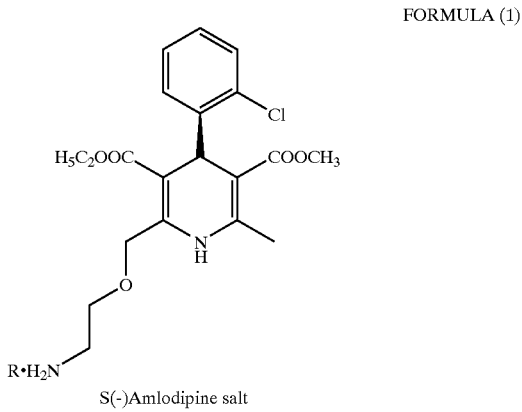

S(-)Amlodipine salt

Wherein R=Benzene sulfonic acid, succinic acid, maleic acid, oxalic acid and p-toluene sulfonic acid, which comprises reacting S (–) amlodipine base with a solution of an acid in presence of an organic solvent at room temperature, adding water to obtain the product in solid form.

In one of the embodiments of the present invention, the organic solvents used for the reaction may be alcohols, hydrocarbons or polar solvents such as dimethyl sulfoxide, 2-propanol, ethanol, methanol and toluene.

In another embodiment the acids used may be benzene sulfonic acid, succinic acid, maleic acid, oxalic acid and p-toluene sulfonic acid.

In another embodiment the acid employed may be 1 mole per mole of amlodipine.

In still another embodiment the water to organic solvent ratio is may be 5:1 to 8:1.

The unique feature of the invention is production of S (−) amlodipine besylate with the quality required for preparation of pharmaceutical composition i.e. tablet formulation.

The process of the present invention is described herein below with reference to examples which are illustrative only and should not be construed to limit the scope of the present invention in any manner.

Optical purity (enantiomeric excess ee) was determined using Chiral HPLC. Ultron chiral chrompak column 15 cm; Flow rate-1 ml/min; Detection wavelength 360 nm;

Mobile phase Disodium hydrogen phosphate buffer (pH 6.9):acetonitrile, 80:20.

$R_t R$=6.1 min., S=7.3 min.

EXAMPLE 1
Amlodipine maleate from S (−) Amlodipine

S (−) Amlodipine (5.0 gms, 0.012 moles, 98.2 ee) was dissolved in ethanol(10 ml) and maleic acid (1.42 gms, 0.012 moles) in 70 ml of water was added with stirring. The separated solid was filtered washed with cold water, washed with hexane and dried under vacuo to give 5.32 gms (82.88%) of S(−) amlodipine maleate, mp. 176–177° C. Optical rotation $[\alpha]^t_D$=−25.10 (c=1, MeOH) 98.3 1ee.

EXAMPLE 2
Amlodipine oxalate from S (−) Amlodipine

S (−) Amlodipine (5.0 gms, 0.012 moles, 98.2 ee) was dissolved in ethanol (10 ml) and oxalic acid (1.54 gms, 0.012 moles) in 70 ml of water was added with stirring. The separated solid was filtered washed with cold water, washed with hexane and dried under vacuo to give 5.80 gms (89.2%) of S(−) amlodipine oxalate. mp. 201–203° C. Optical rotation $[\alpha]^t_D$=−27.95 (c=1, MeOH) 98.41ee.

EXAMPLE 3
Amlodipine succinate from S (−) Amlodipine

S (−) Amlodipine (5.0 gms, 0.012 moles, 98.2 ee) was dissolved in ethanol (10 ml) and succinic acid (1.44 gms 0.012 moles) in 70 ml of water was added with stirring. The separated solid was filtered washed with cold water, washed with hexane and dried under vacuo to give 6.0 gms (93.0%) of S(−) amlodipine succinate, mp. 169–171° C. Optical rotation $[\alpha]^t_D$=−24.55 (c=1, MeOH) 97.95ee.

EXAMPLE 4
Amlodipine tosylate from S (−) Amlodipine

S (−) Amlodipine (5.0 gms, 0.012 moles, 98.2 ee) was dissolved in ethanol (10 ml) and p-toluene sulfonic acid (2.32gms, 0.012 moles) in 70 ml of water was added with stirring. The separated solid was filtered washed with cold water, washed with hexane and dried under vacuo to give 5.32 gms (82.88%) of S(−) amlodipine tosylate, mp. 114–117° C. Optical rotation $[\alpha]^t_D$=−20.2 (c=1, MeOH) 98.23ee.

EXAMPLE 5
Amlodipine besylate from S (−) Amlodipine

S (−) Amlodipine (5.0 gms, 0.012 moles, 98.2 ee) was dissolved in ethanol (10 ml) and benzene sulfonic acid (1.93 gms, 0.012 moles) in 70 ml of water was added with stirring. The separated solid was filtered washed with cold water, washed with hexane and dried under vacuo to give 5.32 gms (82.88%) of S(−) amlodipine besylate, 10 mp. 67–68 softens 107–108° C. Optical rotation $[\alpha]^t_D$=−21.50 (c=1, MeOH) 98.15ee. Microanalysis=C, 50.91%; H, 6.3%; N, 4.67%; S, 5.91%: Calc for $C_{20}H_{24}O_5N_2Cl. C_6H_6O_3S$. 2.5 ($H_2O$), C, 51.1%; H, 5.7%; N, 4.58%; S, 5.24%.

EXAMPLE 6 a) S(−)Amlodipine-besylate from S(−)-Amlodipine

S(−) Amlodipine (62 gms, 0.152 moles, 93.1 ee) was dissolved in isopropanol (62 ml) and a solution of benzene sulfonic acid (24 gm, 0.152 moles) in 50 ml water was added maintaining the temperature ~20° C. The reaction mixture was stirred for 30 min. and distilled water (450 ml) was added. The besylate salt separated after 20 min. stirring continued for one hr. and the slurry was filtered. Washed with distilled water, hexane. The solid was dried under vac. at 40° C. till constant wt. to give S(−) Amlodipine besylate (83 gm, 89% yield) 93.3 ee.

b) Recrystallisation of S(−) Amlodipine besylate

S(−) Amlodipine besylate (80 gms., 93.1 ee) was dissolved in isopropanol (80 ml) The reaction mixture was stirred for 30 min. and distilled water (640 ml) was added. The besylate salt separated after 20 min. stirring continued for one hr. and the slurry was filtered. Washed with distilled water, hexane. The solid was dried under vacuo at 40° C. till constant wt. to give S(−) Amlodipine besylate (63 gm, 98.43 ee).

EXAMPLE 7

S(−)Amlodipine-besylate from S(−)-Amlodipine

S(−) Amlodipine (62 gms, 0.152 moles, 98.2 ee) was dissolved in isopropanol (62 ml) and a solution of benzene sulfonic acid (24 gm, 0.152 moles) in 50 ml water was added maintaining the temperature ~20° C. The reaction mixture was stirred for 30 min. and distilled water (450 ml) was added. The besylate salt separated after 20 min. stirring continued for one hr and the slurry was filtered. Washed with distilled water, hexane. The solid was dried under vacuo at 40° C. till constant wt. to give S(−) Amlodipine besylate (83 gm, 89% yield) 98.3 ee.

Advantages of the Present Invention Are as Follows

The process describes for the first time in detail the preparation of S(−)Amlodipine besylate salt in good chemical yields, high enantiomeric purity and with the quality required for preparation of pharmaceutical composition i.e. tablet formulation.

What is claimed is:

1. A process for the preparation of S(−) Amlodipine salts of general formula (1)

FORMULA (1)

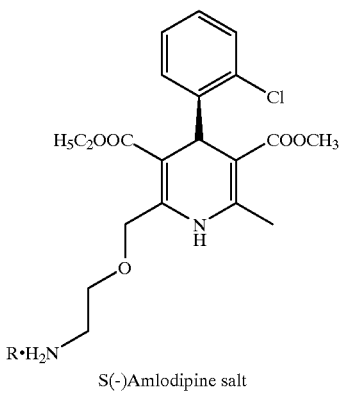

S(-)Amlodipine salt wherein R=Benzene sulfonic acid, succinic acid, maleic acid, oxalic acid and p-toluene sulfonic acid, which comprises reacting S (−) amlodipine base with a solution of an acid in presence of an organic solvent at room temperature, adding water to obtain the product in solid form.

2. A process as claimed in claim 1 wherein the organic solvents used for the reaction may be alcohols, hydrocarbons or polar solvents such as dimethyl sulfoxide, 2-propanol, ethanol, methanol and toluene.

3. A process as claimed in claim 1 wherein the acids used may be benzene sulfonic acid, succinic acid, maleic acid, oxalic acid and p-toluene sulfonic acid.

4. A process claimed in claim 1 wherein the ratio of organic solvent to amlodipine is about one ml/gm of amlodipine.

5. A process claimed in claim 1 where in benzene sulfonic acid is employed about 1 mole per mole of amlodipine.

6. A process claimed in claim 1 wherein water:isopropanol ratio is about 8:1.

\* \* \* \* \*